(12) United States Patent
Nam

(10) Patent No.: US 7,687,062 B2
(45) Date of Patent: Mar. 30, 2010

(54) METHOD FOR DIAGNOSING COLON CANCER

(75) Inventor: Myeong-Jin Nam, Seoul (KR)

(73) Assignee: RNL Bio Co. Ltd., Seoul (KR)

( * ) Notice: Subject to any disclaimer, the term of this patent is extended or adjusted under 35 U.S.C. 154(b) by 0 days.

(21) Appl. No.: 11/838,037

(22) Filed: Aug. 13, 2007

(65) Prior Publication Data

US 2008/0032319 A1 Feb. 7, 2008

Related U.S. Application Data

(63) Continuation-in-part of application No. 11/291,147, filed on Nov. 29, 2005, now abandoned.

(51) Int. Cl.
*G01N 33/00* (2006.01)
*G01N 33/53* (2006.01)
*G01N 33/552* (2006.01)
*G01N 33/553* (2006.01)
*G01N 33/544* (2006.01)
*G01N 33/574* (2006.01)
*A61K 39/00* (2006.01)

(52) U.S. Cl. .................. 424/133.1; 436/501; 436/518; 435/7.1; 435/7.92

(58) Field of Classification Search .............. 424/133.1; 436/501, 518; 435/7.1, 7.92
See application file for complete search history.

(56) References Cited

U.S. PATENT DOCUMENTS

| | | | |
|---|---|---|---|
| 6,180,417 B1 * | 1/2001 | Hajizadeh et al. ............ | 436/518 |
| 2003/0036070 A1 * | 2/2003 | Chakravarti .................... | 435/6 |
| 2004/0265230 A1 * | 12/2004 | Martinez et al. ........... | 424/1.49 |

OTHER PUBLICATIONS

Fundamental Immunology 242 (William E. Paul, M.D. ed., 3d ed. 1993).*
Wehkamp et al. (Digest Dis. & Sci. 47(6):1349-1355 (2002)).*
Fahlgren et al. (Clin. Exp. Immunol. Jan. 2003;131(1):90-101).*
Aksoy et al. (Macromol. Biosci. May 17, 2004;4(5):483-96).*
Myeong J. Nam et al. Indentification of Defensin α6 as a Potential Biomarker in Colon Adenocarcinoma; The Journal of Biological Chemistry vol. 280, No. 9, Issue of Mar. 4, pp. 8260-8265, 2005.
Ruth Ann Bowser-Finn et al. A Comparison of the predictive value and diagnostic efficiency of FHAP and CEA as Cancer Markers; Tumour Biology, 7 (1986) 343-352. Saikon Publishing Co., Ltd.
Eric B. Mallow et al. Human Enteric Defensins, The Journal of Biological Chemistry; vol. 271, No. 8 Issue of Feb. 23, pp. 4038-4045- 1996.
Tomas Ganz et al. Defensins, Natural Peptide Antibiotics of Human Neutrophils; J. Clin. Invest., The American Society for Clinical Investigation, Inc., vol. 76, Oct. 1985, 1427-1435.
Tomas Ganz and Robert I. Lehrer. Defensins, Current Opinion in Immunology 1994, 6:584-589.
Christopher P. Hill et al. Crystal Structure of Defensin HNP-3, an Amphiphillic Dimer: Mechansims of Membrane Permeabilization, Science, Mar. 22, 1991; 251; 5000, ProQuest Medical Library p. 1481-1485.
Monika A. Carpelan-Holmstrom, M.D., et al. Differences in Serum Tumor Markers Between Colon and Rectal Cancer; Comparison of CA 242 and Carcinoembryonic Antigen; The Fourth Department of Surgery, University of Helsinki, Helsinki, Finland, Dis. Colon Rectum 39:799-805 (1996).

* cited by examiner

*Primary Examiner*—Lynn Bristol
(74) *Attorney, Agent, or Firm*—Darby & Darby P.C.

(57) ABSTRACT

The present invention relates to a method for diagnosing colon cancer by detecting a colon cancer specific antigen, defensin α6 from the blood of patient and a diagnostic kit for colon cancer comprising anti-defensin α6 antibody. The diagnostic kit for colon cancer of present invention comprises: a solid support such as 96-well plate for ELISA, nitrocellulose membrane, polyvinylidene fluoride membrane, microplate, glass substrate, polystyrene substrate, silicone substrate or metal plate, on which anti-defensin α6 antibody is immobilized; and, a means for detecting colon cancer specific antigen such as a primary antibody which specifically binds with an antigen conjugated with an antibody on a solid substrate and a secondary antibody-signal complex which specifically binds with the primary antibody. The diagnostic kit of the invention can diagnose colon cancer with the minute amount of patients' blood, which makes possible the easy and simple diagnosis of colon cancer.

14 Claims, 1 Drawing Sheet

US 7,687,062 B2

METHOD FOR DIAGNOSING COLON CANCER

RELATED U.S. APPLICATION DATA

This application is a continuation-in-part of U.S. patent application Ser. No. 11/291,147, filed Nov. 29, 2005.

FIELD OF THE INVENTION

The present invention relates to a method for diagnosing colon cancer and a diagnostic kit there for, more specifically, to a method for diagnosing colon cancer by detecting a colon cancer specific antigen, defensin α6 from the blood of patient and a diagnostic kit for colon cancer comprising anti-defensin α6 antibody.

BACKGROUND OF THE INVENTION

Colorectal cancer is the second leading cause of cancer death in the United States, with 135,000 new cases diagnosed each year and an overall 5-year survival rate of ~50%. Most colorectal cancers develop slowly, beginning as small benign colorectal adenomas that progress over several decades to larger and more dysplastic lesions, eventually becoming malignant. This gradual progression provides ample opportunity for prevention and intervention. Diagnostic screening methods are at present suboptimal; therefore, new approaches are needed.

Early examination for colon cancer is generally performed with the digital rectal examination, sigmoidoscopy, colonoscopy or barium enema.

Digital rectal examination is made to check the normality of colon by an examiner wearing a glove and putting on some lubricant and inserting a hand into the rectum followed by the palpation, sigmoidoscopy is to observe the rectum and colon directly through a long and flexible mirror-attached tube, colonoscopy is to examine inside of the colon directly through an endoscope, and barium enema is to examine the abnormality of the blood stream distributed in the colon after injecting a contrast medium followed by the computed tomography.

The above-mentioned examinations are methods simply to assess the abnormality of the colon and so more precise tissue examination should be followed if lesions of diseases are diagnosed by those methods. For the biopsy performed after identifying lesions of diseases, it is relatively more accurate, but the diagnosis, which accompanies with some pain to patients, is so inconvenient that the patients tend to hesitate to take examinations. Therefore, needs for developing an easy and simple method for diagnosing colon cancer has been continued in the art.

On the other hand, a diagnosis method using genes has been developed for the diseases like cancers occurring genetic mutation and a considerable accomplishment has been reported on lung cancer, liver cancer and stomach cancer, but there are currently not many results reported on colon cancer. The diagnosis using genes is generally performed by PCR using DNA extracted from the tissue suspicious of cancer or by gene expression analysis using cDNA microarray for which RNA is extracted from the tissue. The former is effective only for specific cancers such as chronic myelogenous leukemia (CML) or acute lymphocytic leukemia (ALL) mainly caused by chromosome translocation, and the latter has a drawback that the conventional cancer diagnosis methods such as tissue examination, endoscopy or CT (computerized tomography) scans should precede.

In order to overcome the drawback of the cancer diagnosis methods described above, a method with which detects cancer-specific antigen and diagnoses cancer has been developed. For example, carcinoembryogenic antigen (CEA) has been reported to be a cancer-specific antigen, since the level of CEA is increased in the patients of rectum-colon cancer, stomach cancer, breast cancer, lung cancer, ovary cancer, prostate cancer or pancreas cancer (see: Bowser-Finn, R. A., Kahan, L., Larson, F. C., Traver, M. I. (1986) Tumour Biol. 7, 343-52; Carpelan-Holmstrom, M. A., Haglund, C. H., and Roberts, P. J. (1996) Dis Colon Rectum 39, 799-805). However, even if the cancer patients are diagnosed using CEA, further examination should be made to determine the kind of cancer precisely, which plays a barrier to easy and practical application of CEA in the diagnosis of cancers, since the CEA is commonly expressed in several cancers described above.

In this connection, there are strong reasons for exploring and developing an easy and simple method for diagnosing colon cancer with a high reliability and validity.

SUMMARY OF THE INVENTION

The inventor have made an effort to screen a colon cancer specific antigen and develop a method for diagnosing colon cancer using an antibody against the antigen with a high reliability and validity, and found that colon cancer can be diagnosed by detecting a colon cancer specific antigen, defensin α6 from the blood of colon cancer patients.

One aspect of the present invention is to provide a method for diagnosing colon cancer by detecting a colon cancer specific antigen, defensin α6.

Another aspect of the invention is to provide a diagnostic kit for colon cancer comprising anti-defensin α6 antibody.

In another aspect, the present invention provides a method for detecting colon cancer in a patient. The method comprises contacting blood or serum of the patient with a defensin-α6 monoclonal antibody that binds to defensin-α6.

In a further aspect, the monoclonal antibody is Def-12α.

In yet another aspect of the invention, a method for detecting colon cancer in a patient is provided. The method comprises contacting the blood or serum of the patient with a defensin-α6 monoclonal antibody and assaying the blood or serum to determine whether the antibody bound to the blood or serum.

BRIEF DESCRIPTION OF DRAWINGS

The above and the other objects and features of the present invention will become apparent from the following description given in conjunction with the accompanying drawing, in which.

DETAILED DESCRIPTION OF THE INVENTION

Figure 1:
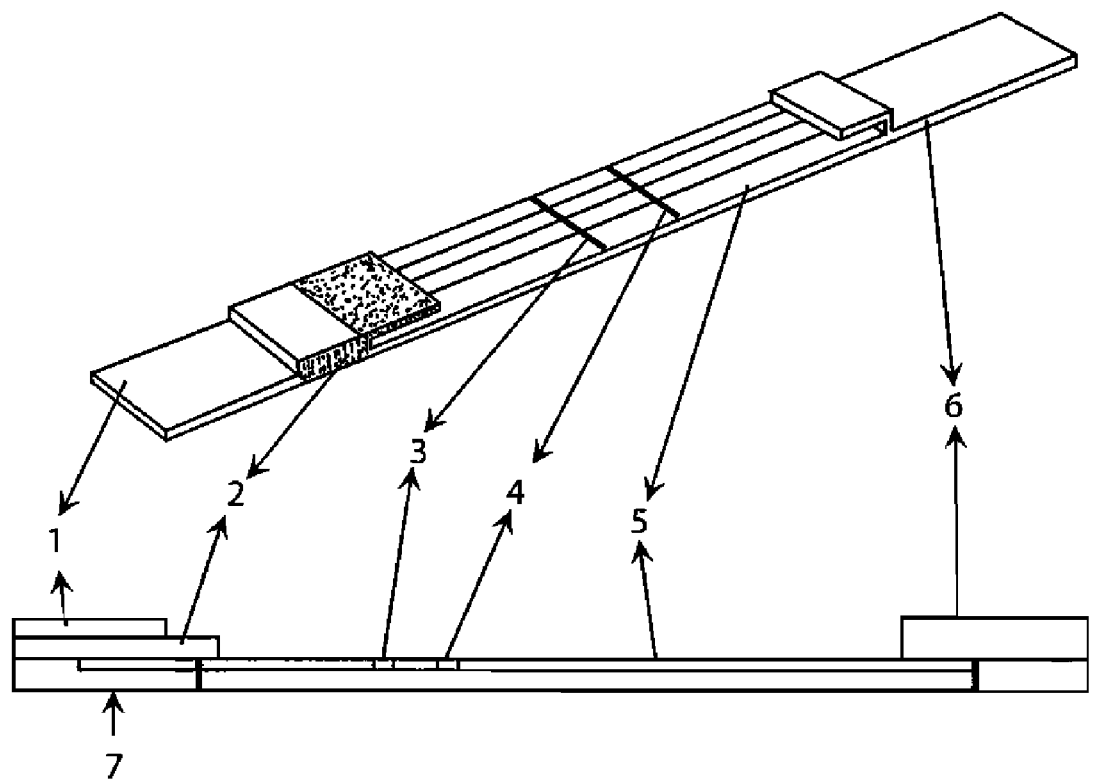
FIG. 1 is a schematic diagram depicting an immunochromatography strip as a preferred embodiment of a diagnostic kit for colon cancer, which comprises a plastic plate (7) on which a sample application pad (1), a gold particle bound anti-defensin α6 antibody temporally immobilized on a glass fiber filter (2), a nitrocellulose membrane (5) on which anti-defensin α6 antibody band (3) and a secondary antibody band (4) are immobilized and an absorbent pad (6) are positioned in a serial manner.

Human defensins comprise a family of closely related, cationic polypeptides 29-42 amino acids in length. The polypeptides contain 6 conserved cysteines linked in disulfide bonds that stabilize the molecules as triple-stranded amphiphilic β-sheet structures (see: Ganz, T and Lehrer, R. I. (1994) Curr. Opin. Immunol. 6, 584-589; Hill, P. C., Yee, J., Selsted, M. E., and Eisenberg, D. (1991) Science 251, 1481-1485). In vitro, human defensins exhibit antimicrobial activity against some bacteria, fungi, enveloped viruses, and parasites. Two classes of human defensins, termed "α-defensins" and "β-defensins", have been identified that differ with respect to their localization and linkage of cysteine residues, precursor peptide structure, and pattern of tissue expression. Whereas β-defensins are most abundant in epithelial cells of the lung, skin, and urogenital tract, the α-defensins were first found in human polymorphonuclear leukocytes and intestinal Paneth cells (see: Ganz, T., Selsted, M. E., Sklarck, D., Harwig, S. S. L., Daher, K., Bainton, D. F., and Lehrer, R. I. (1985) J. Clin. Invest. 76, 1427-1435; Mallow, E. B., Harris, A., Salzman, N., Russell, J. P., DeBerardinis, R. J., Ruchelli, E., and Bevins, C. L. J. Biol. Chem. 271, 4038-4045).

Although defensins seem to have diverse functional activities in innate antimicrobial immunity, a few reports have also indicated the presence of several defensins in epithelial tumors. There is much interest in identification of circulating tumor-derived proteins that may serve as biomarkers for the early detection of colon cancer. The inventor demonstrated that: the defensin α6 (also referred to as defensin 6α) protein is expressed at higher levels in serum from colon cancer patients relative to serum from non-cancer controls; as such, defensin α6 may have utility as a biomarker for colon cancer.

Then, in an effort to identify potential molecular markers of colorectal tumors, the inventor implemented an approach based on the analysis of microarray data for the identification of tumor proteins that may have utility as biomarkers in colon cancer. Expression analysis of microarray data obtained from a variety of 283 tumors and normal tissues revealed that defensin α6 was maximally expressed in colon cancer.

The present inventor obtained tissues from patients suffering from colon cancer, brain cancer, ovary cancer and pancreas cancer, and, from the genes expressed in each of the tissues, screened genes encoding proteins which are expressed in the tissue of colon cancer patient only with no expression in the tissues of the other cancer patients and normal human, and which are secreted to blood of the patients.

From the colon cancer-specific genes, genes encoding extracellular proteins, X14253 (TDGF1), L21998 (Mucin 2) and U33317 (defensin α6), were selected, and Western blot analysis for blood samples from colon cancer patient, normal human and other cancer patients was followed by using an antibody specifically conjugated with proteins expressed by the said genes, which shows that: defensin α6 was detected in the colon cancer patient's serum only; Mucin 2 was detected in the colon cancer patient's serum and other cancer patient's serum; and, TDGF 1 was not detected in the colon cancer patient's serum. Accordingly, it was found that defensin α6 is a colon cancer-specific protein which can be used as a biomarker for diagnosing colon cancer.

One method for diagnosing colon cancer of present invention comprises a step of detecting defensin α6 from the blood of patient, which is expressed in the colon cancer tissue and secreted to blood, where the detection method of defensin α6, not limited thereto, includes immune reaction with anti-defensin α6 antibody, chromatography and electrophoresis.

Another method for diagnosing colon cancer comprises contacting blood or serum of the patient with a defensin-α6 monoclonal antibody that binds to defensin-α6. The method can further comprise assaying the blood or serum of the patient to determine whether the monoclonal defensin-6α antibody bound to defensin α6.

Diagnosing colon cancer of present invention can be practiced by employing a diagnostic kit comprising an anti-defensin 6α antibody or antibodies. Preferably, the diagnostic kit for colon cancer comprises anti-defensin α6 antibody immobilized on a solid support and a means for detecting colon cancer specific antigen conjugated with the said antibody. In various embodiments, the kit comprises monoclonal Def-12α antibody, described in detail in example 5. The hybridoma that produces the Def-12α monoclonal antibody was deposited under Korean Cell Line Research Foundation (KCLRF, address: Seoul National University College of Medicine, 28 Yongon-dong, Chongno-Gu, Seol, 110-744, Korea) deposit number KCLRF-BP-00164 on Aug. 13, 2007.

The solid support, not limited thereto, includes 96-well plate for ELISA, nitrocellulose membrane, polyvinylidene fluoride membrane, microplate, glass substrate, polystyrene substrate, silicone substrate and metal plate.

The means for detecting colon cancer specific antigen, not limited thereto, includes a primary antibody-gold particle conjugate which specifically binds with an antigen conjugated with an antibody on the solid substrate and a primary antibody which specifically binds with an antigen conjugated with an antibody on a solid substrate and a secondary antibody-signal complex which specifically binds with the primary antibody.

The signal, not limited thereto, includes fluorescent material such as Cy-3, Cy-5, FITC (fluoroisothiocyanate), GFP (green fluorescent protein), RFP (red fluorescent protein) and Texas Red, the radioisotope, not limited thereto, includes $^{32}P$, $^{3}H$ and $^{14}C$, and the enzyme, not limited thereto, includes HRP (horseradish peroxidase), alkaline phosphatase, β-galactosidase and luciferase, and in case of using the enzyme as the signal, the kit further comprises a substrate for the enzyme.

As a preferred embodiment of the invention, the kit for diagnosing colon cancer is provided as an ELISA kit comprising anti-defensin α6 antibody. In preferred embodiments, the antibody is Def-12α, a monoclonal antibody specific for defensin α6. Preferably, the kit comprises 96-well plate for ELISA coated with anti-defensin α6 antibody, and a means for detecting defensin α6 such as anti-defensin α6 antibody, and a secondary antibody-signal complex such as HRP (horseradish peroxidase)-conjugated goat anti-rabbit IgG antibody and TMB (tetramethyl benzidine) as a substrate for HRP.

As the other preferred embodiment of the invention, the kit for diagnosing colon cancer is provided as an immunochromatography strip comprising a membrane on which anti-defensin α6 antibody is immobilized, and a means for detecting defensin α6, i.e., a gold particle bound anti-defensin α6 antibody, where the membrane, not limited thereto, includes NC membrane and PVDF membrane. Preferably, it comprises a plastic plate on which a sample application pad, a gold particle bound anti-defensin α6 antibody temporally immobilized on a glass fiber filter, a nitrocellulose membrane on which anti-defensin α6 antibody band and a secondary antibody band are immobilized and an absorbent pad are positioned in a serial manner, so as to keep continuous capillary flow of blood serum.

In case of using the kit as described above, colon cancer patient can be diagnosed by adding blood or blood serum from patient to a diagnostic kit and detecting defensin α6 conjugated with anti-defensin α6 antibody (e.g., Def-12α antibody, disclosed herein), specifically, by a method which comprises the steps of: (i) collecting blood or blood serum from the patient; (ii) separating blood serum from the patient's blood; (iii) adding the blood serum from patient to a diagnostic kit; and, (iv) detecting defensin α6 conjugated with anti-defensin α6 antibody. In this method, the defensin α6 antibodies are brought into contact with the patient's blood. If defensin α6 is present in the sample, the defensin α6 antibodies will bind to the sample, or a portion thereof. In other kit and diagnostic embodiments, blood or blood serum need not be collected from the patient (i.e., it is already collected).

The diagnostic kit of the invention can diagnose colon cancer with a minute amount of patients' blood, which makes possible the easy and simple diagnosis of colon cancer.

The present invention is further illustrated in the following examples, which should not be taken to limit the scope of the invention.

EXAMPLE 1

Screening of Colon Cancer-Specific Genes

The tissues analyzed were consisting of 6 normal brain (BN), 19 brain cancers (BAI), 8 normal colon (CN), 38 microsatellite stability-type colon cancers (CMSS), 13 microsatellite instability-type colon cancers (CMSI), 10 normal lung (LN), 37 lung cancers (LI), 7 normal pancreas (PN), 8 pancreas cancers (PT). Tissues samples were homogenized in the presence of Trizol reagent (Life Technologies, Inc., USA) and total cellular RNA was purified according to manufacturer's procedures. RNA samples were further purified using RNeasy spin columns (Qiagen, USA). RNA quality of the lung and ovary tumors was assessed by 1% agarose gel electrophoresis in the presence of ethidium bromide. Samples that did not reveal intact and approximately equal 18S and 28S ribosomal bands were excluded from this experiment. This experiment used commercially available high-density microarrays (Affymetrix, USA) that produced gene expression levels on 7129 known genes and expressed sequence tags (HuGeneFL Array). Preparation of cRNA, hybridization, and scanning of the arrays were performed according to manufacturer's protocols.

Briefly, 5 μg of the total RNA was used to generate double-stranded cDNA by reverse transcription using a cDNA synthesis kit (Superscript Choice System, Life Technologies, Inc., USA) that uses an oligo(dT)$_{24}$ primer containing a T7 RNA polymerase promotes 3' to the poly T (Geneset, USA), followed by second-strand synthesis. Labeled cRNA was prepared from the double-stranded cDNA by in vitro transcription by T7 RNA polymerase in the presence of biotin-11-CTP and biotin-16-UTP (Enzo, USA). The labeled cRNA was purified over RNeasy columns. 15 μg of cRNA was fragmented at 94° C. for 35 minutes in 40 mmol/L of Tris-acetate, pH 8.1, 100 mmol/L of potassium acetate, and 30 mmol/L of magnesium acetate. The cRNA was then used to prepare 300 μL of hybridization cocktail (100 mmol/L MES, 1 mol/L NaCl, 20 mmol/L ethylenediaminetetraacetic acid, 0.01% Tween 20) containing 0.1 mg/ml of herring sperm DNA (Promega, USA) and 500 μg/ml of acetylated bovine serum albumin (Life Technologies, Inc., USA). Before hybridization, the cocktails were heated to 94° C. for 5 minutes, equilibrated at 45° C. for 5 minutes, and then clarified by centrifugation (16,000×g) at room temperature for 5 minutes. Aliquots of this hybridization cocktail containing 10 μg of fragmented cRNA were hybridized to HuGeneFL arrays at 45° C. for 16 hours in a rotisserie oven for 60 rpm. The arrays were washed using non-stringent buffer (6×SSPE) at 25° C., followed by stringent buffer (100 mmol/L MES, pH 6.7, 0.1 mol/L NaCl, 0.01% Tween 20) at 50° C.

The arrays were stained with streptavidin-phycoerythrin (Molecular Probes, USA), washed with 6× sodium chloride, sodium phosphate, EDTA (SSPE buffer), incubated with biotinylated anti-streptavidin IgG, stained again with streptavidin-phycoerythrin, and washed again with 6×SSPE. The arrays were scanned using the GeneArray scanner (Affymetrix, USA). Image analysis was performed with GeneChip software (Affymetrix, USA), and colon cancer-specific genes expressed in colon cancer tissues were selected by way of quantile-normalization (see: Table 1). As can be seen in Table 1 below, described genes were expressed highly in colon cancer tissues than normal colon as well as other tissues.

TABLE 1

Comparison of Expression Level of Colon Cancer-Specific Genes in Various Cancer Tissues

| Gene** | Tissue* | | | | | | | | |
|---|---|---|---|---|---|---|---|---|---|
| | BN | BAI | CN | CMSS | CMSI | LN | LI | PN | PT |
| U51096 | −19 | 16 | 111 | 1086 | 805 | 21 | 31 | 57 | 31 |
| U22376 | 42 | −9 | −19 | 1956 | 1195 | 127 | 149 | 56 | −31 |
| U51095 | 33 | 93 | 193 | 2474 | 2564 | 58 | 51 | 438 | 179 |
| X14253 | 58 | 65 | 85 | 1349 | 405 | 22 | 57 | 236 | 80 |
| L21998 | 859 | 1037 | 245 | 6139 | 9306 | 893 | 1141 | 1345 | 1057 |
| U30246 | 93 | 29 | 288 | 1374 | 2160 | 70 | 151 | 108 | 80 |
| U33317 | 171 | 149 | 405 | 1494 | 1058 | 59 | 134 | 76 | 31 |
| U79725 | 65 | 26 | 730 | 2622 | 1862 | 345 | 102 | 10 | 49 |
| L02785 | 68 | 67 | 337 | 1710 | 108 | 13 | 32 | 87 | 213 |
| M10050 | −91 | −135 | 2652 | 9101 | 2416 | −148 | −81 | −12 | −68 |
| X83228 | −35 | −27 | 626 | 4641 | 3389 | −45 | 41 | 56 | 147 |
| M30496 | 356 | 341 | 290 | 1954 | 1273 | 382 | 435 | 189 | 478 |
| U26726 | 91 | 43 | 463 | 1882 | 1464 | 97 | 237 | 309 | 347 |
| X12901 | −21 | 13 | 188 | 1578 | 791 | −44 | 183 | 205 | 141 |
| M73489 | 204 | 169 | 362 | 1553 | 987 | 106 | 172 | 686 | 168 |
| M76180 | 6 | 14 | 647 | 2615 | 1300 | 116 | 326 | 580 | 189 |
| L25931 | 166 | 571 | 386 | 2177 | 1665 | 618 | 702 | 341 | 483 |

TABLE 1-continued

Comparison of Expression Level of Colon Cancer-Specific
Genes in Various Cancer Tissues

| Gene** | Tissue* | | | | | | | | |
|---|---|---|---|---|---|---|---|---|---|
| | BN | BAI | CN | CMSS | CMSI | LN | LI | PN | PT |
| U55206 | 117 | 162 | 159 | 2311 | 1149 | 141 | 292 | 38 | 124 |
| M30703 | −26 | 64 | 102 | 1214 | 595 | 487 | 537 | 22 | 239 |

*BN, normal brain tissue; BAI, brain cancer tissue; CN, normal colon tissue; CMSS, MSS (microsatellite stability-type) colon cancer tissue; CMSI, MSI(microsatellite instability-type) colon cancer tissue; LN, normal lung tissue; LI, lung cancer tissue; PN, normal pancreas tissue; PT, pancreas cancer tissue
**The proteins encoded in colon cancer-specific genes are obtained from the manual of Microarray(HuGeneFL Array, Affmetrix, USA): U51096, caudal type homeo box transcription factor 2; U22376, avian myeloblastosis viral oncogene homolog; U51095, caudal type homeo box transcription factor 1; X14253, teratocarcinoma-derived growth factor 1: TDGF1; L21998, intestinal/tracheal mucin 2; U30246, sodium/potassium/chloride transporter; U33317, Paneth cell-specific defensin α6; U79725, trans-membrane glycoprotein A33; L02785, solute carrier family 26, member 3; M10050, fatty acid binding protein 1; X83228, cadherin 17 as liver-intestine cadhedrine; M30496, ubiquitin carboxyl-terminal esterase L3 as ubiquitin thiolesterase; U26726, hydroxysteroid (11-beta) dehydrogenase 2; X12901, villin 1; M73489, guanylate cyclase 2 C as heat stable enterotoxin receptor; M76180, DOPA decarboxylase as aromatic L-amino acid decarboxylase; L25931, lamin B receptor; U55206, gamma-glutamyl hydrolase as folylpolygamma-glutamyl hydrolase; M30703, amphiregulin as schwannoma-derived growth factor.

EXAMPLE 2

Western Blot Analysis

From colon cancer-specific genes in Example 1, genes encoding extracellular proteins, X14253 (TDGF1), L21998 (Mucin 2) and U33317 (defensin α6), were selected, and Western blot analysis for blood samples from a colon cancer patient, normal human and other cancer patient was accomplished by using an antibody specifically conjugated with proteins expressed by the said genes as follows:

Serum was first separated from the blood of patients, who donated normal and cancer tissues in Example 1, and subjected to 10% SDS-polyacrylamide gel electrophoresis, and then transferred to PVDF membrane by electrical means. The PVDF membrane was blocked by incubation for 12-14 hours in a blocking buffer (3% bovine serum albumin, 0.05% Tween 20 in PBS) to reduce non-specific binding of proteins transferred to the membrane. Subsequently, the blocked PVDF membranes were incubated for 2 hours at room temperature with anti-TDGF 1 rabbit polyclonal antibody (Biocat, Germany), anti-Mucin 2 rabbit polyclonal antibody (Abcam, UK) and anti-defensin α6 rabbit polyclonal antibody (Alpha Diagnostic International, USA) at a 1:200(v/v) dilution in the blocking buffer. The membranes was washed in PBST (0.05% Tween 20 in PBS) for 10 minutes three times, and incubated for 45 minutes with horseradish peroxidase-conjugated goat anti-rabbit IgG antibodies (Santa Cruz Biotechnology, USA) at a 1:200(v/v) dilution in the blocking buffer, and then washed in PBS for 10 minutes three times. Immunodetection was accomplished by enhanced chemiluminescence (ECL™ kit, Amersham, UK), followed by PhosphaImager (Fuji, Japan).

As a result, defensin α6 and Mucin 2 were detected in the colon cancer patient's serum, while TDGF 1 was not detected, indicating that defensin α6 is a colon cancer-specific protein which can be used as a biomarker for diagnosing colon cancer.

EXAMPLE 3

Preparation of ELISA Kit for Diagnosing Colon Cancer and Analysis of Blood Sample Using the Kit

EXAMPLE 3-1

Preparation of ELISA Kit for Diagnosing Colon Cancer

An ELISA kit for diagnosing colon cancer was prepared to comprise a 96-well plate for ELISA, anti-defensin α6 rabbit polyclonal antibody, HRP (horseradish peroxidase)-conjugated goat anti-rabbit IgG antibody and TMB (tetramethyl benzidine).

A 96-well maxi-sorp microtiter plate (Nunc, USA) was coated by incubation overnight at 4° C. with anti-defensin α6 rabbit polyclonal antibody (5 μL/well) at a 1:50(v/v) dilution in a coating buffer ($Na_2CO_3$ 0.188% (w/v), $NaHCO_3$ 0.271% (w/v), NaCl 0.731% (w/v), pH 9.6). After washing in PBS three times, the coated wells were blocked by incubation for 1 hour at 4° C. in a blocking buffer (3% (w/v) BSA, 0.05% (w/v) Tween 20 in PBS) to block non-specific binding, and dried and sealed up to prepare a 96-well plate for ELISA kit.

Then, commercially available anti-defensin α6 antibody, HRP (horseradish peroxidase)-conjugated goat anti-rabbit IgG antibody (Alpha Diagnostic International, USA) and TMB (tetramethyl benzidine) (Sigma Chem. Co., USA), all of which are used together with the 96-well plate for ELISA kit.

EXAMPLE 3-2

Analysis of Blood Sample

200 µL of serum of a colon cancer patient, pancreas cancer patient, ovary cancer patient, brain cancer patient and normal human were added to each well of ELISA plate prepared in Example 3-1. After the first antigen-antibody interaction was accomplished by mild shaking the plate for 1 hour at room temperature, the serum was removed from each well, and the wells were then washed 5× in PBS.

Subsequently, 50 µL of the anti-defensin α6 polyclonal antibody at a 1:200(v/v) dilution in PBST was added to each well in which the primary antigen-antibody interaction was accomplished, and the second antigen-antibody interaction was accomplished for 2 hours at room temperature, and the wells were then washed three times in PBST. The wells were then blocked by incubation for 1 hour at room temperature to block non-specific conjugation. And then, 50 µL of HRP-conjugated goat anti-rabbit IgG at a 1:400 dilution in the blocking buffer was added to each well in which the secondary antigen-antibody interaction was accomplished, and incubated by slow shaking for 2 hours at room temperature.

The said plate was washed four times in PBST, and a coloring agent, TMB (tetramethyl benzidine, Sigma Chem. Co., USA) was added to the plate at a concentration according to manufacturer's protocols, and then added 1.25M $H_2SO_4$ to stop the color reaction. Subsequently, the wells were read at 450 nm using a microtiter plate reader (Model 680 Microplate Reader, Biorad, USA) (see: Table 2).

an immune reaction member: AuCl (gold monochloride) was treated with sodium citrate solution to give a solution containing reduced gold particle with a particle size of 40 nm having an optical density of 10±1 at 532 nm. To AuCl solution was added anti-defensin α6 antibody at a concentration of 10 µg/ml and added PEG (polyethylene glycol) to obtain a primary antibody-gold particle conjugate solution. Subsequently, the glass fiber filter (0.8 cm×1.0 cm, Millipore, USA) was impregnated with the antibody-gold particle conjugate solution and dried at 37° C., finally to prepare an immune reaction member.

EXAMPLE 4-3

Preparation of Result Indicator

NC membrane was cut to have a size of 0.8 cm×5 cm, and a decision line was created in a position of 0.8 cm apart from the lower end of the membrane in the length direction and the control line was created in a position of 0.8 cm apart from the decision line in the upper direction, to give a result indicator in a form of NC membrane: The decision line was created in a straight line using a mixture of anti-defensin α6 antibody and PBST at a 1:50(v/v) dilution and dried at 37° C., and the control line was created in a straight line using a mixture of

TABLE 2

ELISA Results of Serum Samples from Normal Human and Patients Suffering from Various Cancers (unit: absorbance at 450 nm)

| Cancer-specific Antigen | Normal human | Colon cancer | Pancreas cancer | Ovary cancer | Brain cancer |
|---|---|---|---|---|---|
| Defensin α6 | 0.083 ± 0.016 | 0.251 ± 0.039 | 0.075 ± 0.021 | 0.078 ± 0.024 | 0.091 ± 0.031 |

As can be seen in Table 2 above, it was clearly demonstrated that the level of defensin α6 in colon cancer patient was higher more than double than that in normal human and other cancers patients, indicating that the ELISA kit can be used for the diagnosis of colon cancer with a high reliability and validity.

EXAMPLE 4

Preparation of Immunochromatography Strip for Diagnosing Colon Cancer and Analysis of Blood Sample

EXAMPLE 4-1

Preparation of Sample Application Pad

Cellulose filter (Millipore, USA) was cut in a size of 0.8 cm×1.2 cm to prepare a sample application pad for immunochromatography strip.

EXAMPLE 4-2

Preparation of Immune Reaction Member

A gold particle bound anti-defensin α6 antibody was immobilized on a glass fiber (GF) filter temporally to prepare goat anti-rabbit IgG (Santa-Cruz, USA) and PBST at a 1:50 (v/v) dilution and dried at 37° C.

EXAMPLE 4-4

Preparation of Absorbent Pad

A cellulose filter (Millipore, USA) was cut to have a size of 0.8 cm×3 cm to prepare an absorbent pad, which allows continuous capillary flow of blood sample by absorbing non-reactive materials after immune reaction.

EXAMPLE 4-5

Preparation of Immunochromatography Strip for Diagnosing Colon Cancer

On a plastic plate having a size of 0.8 cm×12 cm (Millipore, USA), the sample application pad prepared in Example 4-1, the immune reaction member prepared in Example 4-2, the result indicator prepared in Example 4-3 and the absorbent pad prepared in Example 4-4 were positioned serially in the length direction, to prepare an immunochromatography strip for diagnosing colon cancer. The sample application pad, immune reaction member, result indicator and absorbent pad are positioned, in a manner that the said components overlapped one another to keep continuous capillary flow of liquid sample. FIG. 1 is a schematic diagram depicting an immunochromatography strip for colon cancer, which comprises a plastic plate (7) on which a sample application pad (1), a gold particle bound anti-defensin α6 antibody temporally immobilized on a glass fiber filter (2), a nitrocellulose membrane (5) on which anti-defensin α6 antibody band (3) and a secondary antibody band (4) are immobilized and an absorbent pad (6) are positioned in a serial manner, so as to keep continuous capillary flow of blood serum.

EXAMPLE 4-6

Analysis of Blood Samples

Blood samples were collected from 5 normal humans, 7 colon cancer patients, 5 pancreas cancer patients, 4 ovary cancer patients and 3 brain cancer patients, and 3 mL of each blood samples was added to the sample application pad of the immunochromatography strip prepared in Example 4-5. After five minutes, it was examined whether gold particle conjugates in decision line were detected or not. As a result, it was found that only in the blood samples of colon cancer patients, gold particle conjugates were detected in decision line.

Therefore, the immunochromatography strip of the invention can diagnose colon cancer, which makes possible the easy diagnosis of colon cancer with a high reliability and validity.

EXAMPLE 5

Production and Validation of Defensin α6 Monoclonal Antibody

Materials & Methods

Hybridoma Production and Selection

A recombinant defensin protein was prepared using cloning defensin 6α cDNA. Female BALB/c pups were injected intra-peritoneally with 100 μg of a recombinant defensin protein per mice with complete Freund's adjuvant at the week 0. After 4 weeks, incomplete Freund's adjuvant was mixed with a recombinant defensin protein and injected intra-peritoneally. It was repeated at the 6 and 8 weeks with bleeding. The fusion was performed using the SP2/0 mouse myeloma cell line at the week 13 with the following schedules; fusion ELISA at 15 weeks, screening at 16 weeks, 1st cloning at 17 weeks, screening at 19 weeks, 2nd cloning at 20 weeks, screening at 22 weeks, 3rd cloning at 23 weeks, screening at 25 weeks, freezing at 26 weeks, final screening at 27 weeks, ascites collection at 31 weeks.

Supernatants from rapidly growing clones were initially screened by enzyme-linked immunosorbent assay (ELISA) using the Lovo cells as the reactive line and the Raji lymphoblastoma line as a negative control. Briefly, Lovo cells were grown in 96-well plates (Costar, Cambridge, Mass.) until confluent and then fixed for 15 min. in a 0.15% glutaraldehyde/PBS solution. Raji cells being non-adherent were immobilized onto poly-L-lysine coated 96 well plates using $10\text{-}12\times10^6$ cells per plate. Plates were centrifuged to adhere the Raji cells to well bottoms, after which the cells were fixed with glutaraldehyde in a manner identical to that for the Lovo cells. After fixation the plates were blocked with 2% BSA/PBS for 1 hr. at room temperature. The hybridoma supernatants (50 mL) were added and incubated for 30 min. at room temperature. After washing, 50 mL of mouse IgG specific biotinylated horse anti-mouse antibody (BA-2080; Vector Laboratories, Burlingame, Calif.) was added at 2 mg/mL in 33% horse serum in 0.1% BSA/PBS and incubated for 30 min at room temperature. Controls consisted of MOPC-21, a IgG1 monoclonal antibody with no reactivity to human antigens as a negative hybridoma supernatant control and serum from the mouse providing the spleen for fusion as a positive control. The Vectastain ABC kit (Vector Laboratories) and ABTS substrate (Zymed Laboratories, South San Francisco, Calif.) were used for the detection component of the ELISA. The supernatants which reacted to the Lovo cells but not to the Raji cells were identified and the respective hybridoma cultures were selected and further screened by immunohistochemistry against colon and other tissues. Highly reactive clones were subcloned and rescreened a minimum of three times. Hybridomas that remained positive by immunohistochemistry were recloned and used for ascites production. Monoclonal antibody isotypes were determined with the Isostrip isotyping kit (Boehringer Mannheim, Indianapolis, Ind.).

Ascites and Monoclonal Antibody Purification

BALB/c mice were primed with incomplete Freund's adjuvant two weeks prior to i.p. injection of $3\times10^6$ actively growing hybridomas. Ascitic fluid was collected and incubated at 37° C. for 1 h, then at 4° C. overnight. On the following day, the ascitic fluid was centrifuged at 300×g for 20 min., the lipid layer was removed, and the ascites was stored at −20° C. Prior to immunoglobulin purification, the ascitic fluid was treated with BPA 1000 Biocryl beads (TosoHaas Bioseparation Specialists, Montgomeryville, Pa.) to remove contaminating lipids, nucleic acids, and cell debris. The IgG1 monoclonal antibodies (Mabs) were isolated from the ascites using a recombinant protein A column (Unisyn Technologies, Tustin, Calif.).

Immunoperoxidase (IP) Staining

Frozen tissue sections of 5 mm thickness were prepared on poly-L-lysine coated slides (Sigma Chemical Co., St. Louis, Mo.) and fixed in ice-cold acetone for 15 min. The sections were treated for 15 min. with 0.03% $H_2O_2$ to quench endogenous peroxidase and then blocked with 4% horse serum plus 4.8% chicken serum in PBS to prevent non-specific binding of the secondary antibody. An Avidin/Biotin Blocking kit (Vector Laboratories) was used to block endogenous biotin. The primary Mab was added at 10 mg/mL and incubated for 30 min. at room temperature, followed by washing and addition of the biotinylated horse anti-mouse secondary antibody in 10% horse serum at 7.5 mg/mL. The secondary antibody was allowed to react for 30 min. at room temperature, after which any unbound secondary antibody was removed by washing. Detection of the bound secondary antibody was accomplished with the Vectastain ABC kit (Vector Laboratories) and DAB (Research Genetics, Huntsville, Ala.) as the substrate. Tissues were counterstained with hematoxylin.

ELISA

Reactivity of defensin to twenty four human carcinoma cell lines and human white blood cells was assessed by ELISA. Mabs MOPC-21 and polyclonal defensin antibody were used as controls.

Indirect Immunofluorescent (IDIF) Staining

Twenty four human tumor cell lines were used in these studies. To determine the stability of antigen expression, Lovo cells were treated with 0.25% trypsin, 0.5 mM EDTA, 0.01% collagenase, or 0.01% hyaluronidase prior to staining. All cell lines were removed from flasks by scraping and washed in PBS. An aliquot containing $5\times10^5$ cells was removed and pelleted by centrifugation. These cells were resuspended in 200 mL of the primary antibody at 10 mg/mL. The resulting suspension was incubated for 30 min. at room temperature. The cells were washed in PBS and resuspended with a fluorescein-conjugated goat anti-mouse antibody (Biosource International, Camarillo, Calif.) at 10 mg/mL and incubated for 30 min at room temperature. The cells were washed with PBS, resuspended in HBSS and mounted in a 1:1 solution of n-propyl gallate glycerol (5% w/v in HBSS) which reduces light-induced bleaching. A total of 300 cells were counted and evaluated per cell line.

Sensitivity of Monoclonal Def-12α to Defensin 6α Compared with Polyclonal Antibody DEF-6α

A tissue microarray (TMA) with samples of colon adenocarcinoma were stained with Def-12α and DEF-6α.

Results

Hybridoma Production and Selection

Following the initial screening of supernatants by ELISA, seven hybridoma clones highly reactive to Lovo cells and not to Raji cells were selected for further evaluation. After two rounds of cloning and subsequent screening by immunohistology using a panel of embedded human tissues, the Mab designated Def-12α was shown to have the highest specificity for colon. The Def-12α hybridomas were cloned another two times and the cells were then used for the production of antibody in ascites. The Def-12α hybridoma cell line was deposited in the Korean Cell Line Research Foundation (KCLRF, address: Seoul National University College of Medicine, 28 Yongon-dong, Chongno-Gu, Seol, 110-744, Korea) deposit number KCLRF-BP-00164 on Aug. 13, 2007. Isotyping revealed that Mab Def-12α was an IgG1 antibody. Purified Def-12α antibody from ascetic fluid was used for all of the studies described here.

Immunoperoxidase Staining

Mab Def-12α reacted with all colon carcinoma (N=20) (Table 3). Cellular staining was localized to the luminal epithelium and varied in intensity from 1-4 based on a scale of 0-4, where 0=no staining and 4=very dark staining. The percentage of epithelial cells stained with Def-12α ranged from 15-30% (median: 20%) in the sections of normal colon, and from 50-99% (median: 90%) in sections of colon cancer. Table 3 also provides Mab Def-12α reactivity results using a panel of 45 normal human tissue samples (15 types) and four non-prostate carcinomas. Mab 107-1A4 did not react to any tissues in the panel with two minor exceptions, minimal reactivity was observed to normal stomach and small intestine.

TABLE 3

Reactivity to human tissues by IP staining

| Tissues | Positive/total | Intensity | Cells stained(%) |
|---|---|---|---|
| Colon adenocarcinoma | | | |
| Moderately differentiated | 12/12 | 2-4 | 50-99 |
| Poorly differentiated | 6/6 | 2-4 | 60-99 |
| Metastatic colon carcinoma | 2/2 | 4 | 99 |
| Colon adenoma | 5/22 | 0-2 | 15-30 |
| Normal | | | |
| Liver | 0/3 | 0 | 0 |
| Pancreas | 0/3 | 0 | 0 |
| Muscle | 0/3 | 0 | 0 |
| Skin | 0/3 | 0 | 0 |
| Lymph nodes | 0/3 | 0 | 0 |
| Breast | 0/3 | 0 | 0 |

TABLE 3-continued

Reactivity to human tissues by IP staining

| Tissues | Positive/total | Intensity | Cells stained(%) |
|---|---|---|---|
| Bladder | 0/3 | 0 | 0 |
| Kidney | 0/3 | 0 | 0 |
| Lung | 0/3 | 0 | 0 |
| Ureter | 0/3 | 0 | 0 |
| Small intestine | 1/3 | 1 | 20 |
| Stomach | 1/3 | 1 | 20 |
| Tonsil | 0/3 | 0 | 0 |
| Spleen | 0/3 | 0 | 0 |
| Seminal vesicle | 0/3 | 0 | 0 |
| Non-colon cancers | | | |
| Testicular | 0/4 | 0 | 0 |
| Bladder | 0/2 | 0 | 0 |
| Renal cell | 0/5 | 0 | 0 |
| Prostate | 0/3 | 0 | 0 |

ELISA

A panel of 24 cell lines encompassing 11 types of tumors plus white blood cells from normal donors were screened by ELISA for reactivity with Mab Def-12α (Table 4). Of the 24 lines tested colon adenocarcinoma cells gave positive reactions with Def-12α.

IDIF

The reactivity of Def-12α with the 24 individual cell lines used in the ELISA panel was also evaluated by IDIF (Table 2). Similar reactivities were observed. Def-12α reacted strongly to the surface of Lovo, SW620, HT-29, LS 174T cells. The staining appeared as a bright halo around the surface of each of the cells. However, no reactivity was observed with any other lines in the panel.

TABLE 4

Reactivity to human cell lines by ELISA and IDIF

| Cell line | Type | ELISA ± | IDIF staining ± | Positive cells(%) |
|---|---|---|---|---|
| Lovo | Colon adenocarcinoma | + | + | 100 |
| SW620 | Colon adenocarcinoma | + | + | 100 |
| HT-29 | Colon adenocarcinoma | + | + | 100 |
| LS 174T | Colon adenocarcinoma | + | + | 100 |
| DU 145 | Prostate carcinoma | − | − | 0 |
| PC-3 | Prostate carcinoma | − | − | 0 |
| T24 | Bladder carcinoma | − | − | 0 |
| J82 | Bladder carcinoma | − | − | 0 |
| 5637 | Bladder carcinoma | − | − | 0 |
| 486P | Bladder carcinoma | − | − | 0 |
| Caki-2 | Renal cell carcinoma | − | − | 0 |
| 7860 | Renal cell carcinoma | − | − | 0 |
| ACHN | Renal cell carcinoma | − | − | 0 |
| 769P | Renal cell carcinoma | − | − | 0 |
| SK-MES-1 | Squamous cell lung carcinoma | − | − | 0 |
| A-427 | Carcinoma of the lung | − | − | 0 |
| MCF7 | Breast adenocarcinoma | − | − | 0 |
| Hep G2 | Hepatocellular carcinoma | − | − | 0 |
| SK-MEL-24 | Melanoma | − | − | 0 |
| Malme | Melanoma | − | − | 0 |
| 833K | Testicular carcinoma | − | − | 0 |
| 1411H | Testicular carcinoma | − | − | 0 |
| A431 | Ovarian carcinoma | − | − | 0 |
| Raji | Lymphoblastoma | − | − | 0 |
| WBC | Human white blood cells | − | − | 0 |

Sensitivity of Monoclonal Def-12α to Defensin 6α Compared with Polyclonal Antibody DEF-6α

Studies using a monoclonal (Def-12α) and a polyclonal antibody (DEF-6α) to defensin 6α have shown variable binding to defensin α6, expressed in colon cancer. The goal of this experiment is to compare the sensitivity of both antibodies in colon cancers. Ninety percent of colon adenocarcinoma (88/96) showed predominantly strong Def-12α binding while 39% (35/89) showed variable DEF6α binding (sensitivity 90% versus 39%, P<0.05) (Table 5). Differences between Def-12α and DEF-6α appear dramatic and clinically significant. Def-12α may offer significant advantage in diagnosis of colon cancer because of its superior affinity as compared to the polyclonal antibody.

TABLE 5

Defensin 6α expression in tissue microarray colon cancer samples

| Antibody type | Total samples | Moderate-strong expression (binding) | Weak expression (binding) | Negative |
|---|---|---|---|---|
| Def-12α (monoclonal) | 96 | 80 (84%) | 8 (8%) | 8 (8%) |
| DEF6α (commercially available polyclonal) | 89 | 20 (22%) | 15 (17%) | 54 (61%) |

As clearly illustrated and demonstrated as above, the present invention provides a method for diagnosing colon cancer by detecting a colon cancer specific antigen, defensin α6 from the blood of patient and a diagnostic kit therefore. The diagnostic kit of the invention can diagnose colon cancer with the minute amount of patients' blood, which makes possible the easy and simple diagnosis of colon cancer.

What is claimed is:

1. A hybridoma cell line Def-12α deposited with the Korean Cell Line Research Foundation under accession number KCLRF-BP-00164.

2. A monoclonal antibody Def-12α, immunoreactive with defensin-α6, wherein the monoclonal antibody Def-12α is produced by the hybridoma of claim 1.

3. A kit which comprises the anti-defensin-α6 antibody Def-12α of claim 2 immobilized on a solid support, and a defensin-α6 antigen detection means conjugated to said antibody.

4. The kit of claim 3, wherein the solid support is selected from the group consisting of a 96-well plate for ELISA, a nitrocellulose membrane, a polyvinylidene fluoride membrane, a microplate, a glass substrate, a polystyrene substrate, a silicone substrate and a metal plate.

5. The kit of claim 3, wherein the defensin-α6 antigen detection means is a primary antibody-gold particle conjugate which specifically binds with defensin-α6 conjugated with Def-12α on the solid support.

6. The kit of claim 3, wherein the defensin-α6 antigen detection means comprises a primary antibody which specifically binds with defensin-α6 conjugated with Def-12α on the solid support and a secondary antibody-signal complex which specifically binds with the primary antibody.

7. The kit of claim 6, wherein the signal is a fluorescent material, a radioisotope or an enzyme.

8. The kit of claim 7, wherein the fluorescent material is selected from the group consisting of Cy-3, Cy-5, FITC (fluoroiso thiocyanate), GFP (green fluorescent protein), RFP (red fluorescent protein) and Texas Red.

9. The kit of claim 7, wherein the enzyme is selected from the group consisting of HRP (horseradish peroxidase), alkaline phosphatase, β-galactosidase and luciferase.

10. An ELISA kit which comprises a 96 well plate for ELISA coated with the monoclonal Def-12α antibody of claim 2 and an anti mouse IgG secondary antibody.

11. An immunochromatography strip for detecting defensin-α6 comprising a membrane on which the Def-12α antibody of claim 2 is immobilized, and a defensin-α6 detection means.

12. The immunochromatography strip of claim 11, wherein the membrane is a NC membrane or a PVDF membrane.

13. The immunochromatography strip of claim 11, wherein the defensin-α6 detection means is a gold particle bound anti-defensin-α6 antibody.

14. An immunochromatography strip for detecting defensin-α6 comprising a plastic plate on which a sample application pad, a gold particle bound Def-12α antibody of claim 2 immobilized on a glass fiber filter, a nitrocellulose membrane on which anti-defensin-α6 antibody band and a secondary antibody band are immobilized, and an absorbent pad are positioned in a serial manner.

* * * * *